US010729849B2

(12) United States Patent
Finan et al.

(10) Patent No.: US 10,729,849 B2
(45) Date of Patent: Aug. 4, 2020

(54) INSULIN-ON-BOARD ACCOUNTING IN AN ARTIFICIAL PANCREAS SYSTEM

(71) Applicant: LifeSpan IP Holdings, LLC, Malvern, PA (US)

(72) Inventors: Daniel Finan, Philadelphia, PA (US); Pavel Vereshchetin, Moscow (RU)

(73) Assignee: LifeSpan IP Holdings, LLC, Malvern, PA (US)

( * ) Notice: Subject to any disclaimer, the term of this patent is extended or adjusted under 35 U.S.C. 154(b) by 447 days.

(21) Appl. No.: 15/481,514

(22) Filed: Apr. 7, 2017

(65) Prior Publication Data
US 2018/0289891 A1    Oct. 11, 2018

(51) Int. Cl.
| | | |
|---|---|---|
| *A61M 5/172* | (2006.01) | |
| *G05B 13/04* | (2006.01) | |
| *G16H 20/17* | (2018.01) | |
| *G16H 50/50* | (2018.01) | |
| *G16H 40/63* | (2018.01) | |
| *A61M 5/142* | (2006.01) | |

(52) U.S. Cl.
CPC ......... *A61M 5/1723* (2013.01); *G05B 13/048* (2013.01); *G16H 20/17* (2018.01); *G16H 40/63* (2018.01); *G16H 50/50* (2018.01); *A61M 5/14244* (2013.01); *A61M 5/14248* (2013.01); *A61M 5/14276* (2013.01); *A61M 2005/14208* (2013.01); *A61M 2005/1726* (2013.01); *A61M 2205/3561* (2013.01); *A61M 2205/505* (2013.01); *A61M 2230/201* (2013.01)

(58) Field of Classification Search
CPC ................ A61M 5/1723; A61M 5/142; A61M 2005/14208; A61M 2005/14276; A61M 2005/1726; A61M 2230/201; G16H 20/17
See application file for complete search history.

(56) References Cited

U.S. PATENT DOCUMENTS 6,544,212 B2 *  4/2003  Galley ............... A61B 5/14532
                                                             604/31
7,060,059 B2    6/2006  Keith et al.
(Continued)

FOREIGN PATENT DOCUMENTS

WO    2012051344 A2    4/2012

OTHER PUBLICATIONS

Atlas et al., "MD-Logic Artificial Pancreas System," Diabetes Care, vol. 33, No. 5, May 2010.
(Continued)

*Primary Examiner* — Lauren P Farrar

(57) ABSTRACT

An artificial pancreas system includes a continuous glucose monitoring device, a drug delivery device configured to exchange data with the continuous glucose monitoring device and containing a control algorithm, and possibly a remote controller configured to exchange data with the drug delivery device. The algorithm contains an insulin-glucose model, but is decoupled mathematically from the insulin injected by the user to offset the ingested carbohydrates. The control algorithm is designed to calculate two versions of insulin-on-board-patient-facing insulin-on-board (PFIOB) and system-facing insulin-on-board (SFIOB) to properly parse boluses and inform the system of only the insulin that is intended for high glucose correction, but not carbohydrate offsetting.

21 Claims, 6 Drawing Sheets

(56) References Cited

U.S. PATENT DOCUMENTS

| | | | |
|---|---|---|---|
| 7,553,281 B2* | 6/2009 | Hellwig | G06F 19/3468 |
| | | | 600/365 |
| 8,974,439 B2 | 3/2015 | Estes | |
| 2011/0257627 A1 | 10/2011 | Hovorka | |
| 2011/0313680 A1 | 12/2011 | Doyle, III et al. | |
| 2012/0150144 A1* | 6/2012 | Campbell | A61M 5/14244 |
| | | | 604/504 |
| 2012/0232520 A1* | 9/2012 | Sloan | A61B 5/14532 |
| | | | 604/504 |
| 2013/0165901 A1* | 6/2013 | Ruchti | A61M 5/1723 |
| | | | 604/504 |
| 2014/0005633 A1* | 1/2014 | Finan | A61M 5/1723 |
| | | | 604/504 |
| 2014/0066892 A1* | 3/2014 | Keenan | A61M 5/172 |
| | | | 604/506 |
| 2014/0107607 A1* | 4/2014 | Estes | A61M 5/1452 |
| | | | 604/500 |
| 2014/0200426 A1* | 7/2014 | Taub | A61B 5/14532 |
| | | | 600/347 |
| 2014/0276574 A1 | 9/2014 | Saint | |
| 2016/0317743 A1* | 11/2016 | Estes | A61M 5/1723 |
| 2017/0220751 A1* | 8/2017 | Davis | A61B 5/0015 |

OTHER PUBLICATIONS

Cobelli et al., "Artificial Pancreas: Past, Present, Future" Diabetes vol. 60, Nov. 2011.

Kovatchev et al., "Control to Range for Diabetes: Functionality and Modular Architecture," J. Diabetes Sci. Techn., vol. 3, Issue 5, Sep. 2009.

Lee et al., "A Closed-Loop Artificial Pancreas based on MPC: Human Friendly Identification and Automatic Meal Disturbance Rejection," Proceedings of the 17th World Congress, The International Federation of Automatic Control, Seoul Korea Jul. 6-11, 2008.

Lee et al., "A Closed-Loop Artificial Pancreas Using Model Predictive Control and a Sliding Meal Size Estimator" J. Diabetes Sci. Techn., vol. 3, Issue 5, Sep. 2009.

Magni et al., "Model Predictive Control of Type 1 Diabetes: An in Silico Trial" J. Diabetes Sci. Techn., vol. 1, Issue 6, Nov. 2007.

Magni et al., "Run-to-Run Tuning of Model Predictive Control for Type 1 Diabetes Subjects: in Silico Trial" J. Diabetes Sci. Techn., vol. 3, Issue 5, Sep. 2009.

Soru et al., "MPC Based Artificial Pancreas; Strategies for Individualization and Meal Compensation," Annual Reviews in Control 36, p. 118-128 (2012).

Percival et al., "Closed-Loop Control and Advisory Mode Evaluation of an Artificial Pancreatic Beta Cell: Use of Proportional-Integral-Derivative Equivalent Model-Based Controllers" J. Diabetes Sci. Technol., vol. 2, Issue 4, Jul. 2008.

Percvial et al., "Closed-Loop Control of an Artificial Pancreatic β-Cell Using Multi-Parametric Model Predictive Control," Diabetes Res. 2008.

Wang et al., "Automatic Bolus and Adaptive Basal Algorithm for the Artificial Pancreatic β-Cell" Diabetes Techn. Ther., vol. 12, No. 11, 2010.

International Search Report and Written Opinion issued in corresponding International Patent Application No. PCT/US2018/26206, dated Jul. 6, 2018, 10 pages.

* cited by examiner

INSULIN-ON-BOARD ACCOUNTING IN AN ARTIFICIAL PANCREAS SYSTEM

TECHNICAL FIELD

The invention is directed, generally, to the field of glucose management systems and more specifically to a closed-loop glucose management system, such as an artificial pancreas system, that employs a controller that uses more than one model to account for insulin-on-board.

BACKGROUND

Diabetes mellitus is a chronic metabolic disorder caused by an inability of the pancreas to produce sufficient amounts of the hormone insulin resulting in a decreased ability of the body to metabolize glucose. This failure can lead to excessive glucose in the blood stream, or hyperglycemia. Persistent hyperglycemia alone or in combination with hypoinsulinemia is associated with a variety of serious symptoms and life threatening long term complications. Currently, restoration of endogenous insulin production is not yet possible. As a result, therapy is required to help keep blood glucose concentrations within a normal range. Such glycemic control is achieved by regularly supplying external insulin to the body of the patient to reduce levels of blood glucose.

Considerable advancements have been made in diabetes treatment and therapy by the development of drug delivery devices that relieve the need for the patient to use syringes or drug pens to administer multiple daily injections of insulin. These drug delivery devices allow for the delivery of insulin in a manner that is more comparable to the naturally occurring insulin release by the human pancreas and that can be controlled to follow different standards or individually modified protocols to give the patient more customized glycemic control.

These drug delivery devices can be constructed as implantable devices. Alternatively, the device may be an external device with an infusion set for subcutaneous infusion to the patient via the transcutaneous insertion of a catheter, cannula, or transdermal drug transport, such as through a patch. The external drug delivery devices are mounted on clothing or, more preferably, hidden beneath or inside clothing or mounted on the body, and are generally controlled through a user interface built-in to the device or provided on a separate remote device.

Blood or interstitial glucose monitoring is required to achieve acceptable glycemic control with the devices. For example, delivery of suitable amounts of insulin by the drug delivery device requires that the user frequently, episodically, determines his or her blood glucose level by testing. The level is input into the pump or a controller, after which suitable modification may be calculated to the default or currently in-use insulin delivery protocol (i.e., dosage and timing). Such modification is used to adjust the drug delivery device operation accordingly. Alternatively, or in conjunction with such episodic determinations, continuous glucose monitoring ("CGM") is used with the drug delivery device and allows for closed-loop control of the insulin being infused into the diabetic patient.

Further, and to allow for closed-loop control, autonomous modulation of drug being delivered to the user is provided by a controller using one or more control algorithms. For example, proportional-integral-derivative algorithms ("PID") that are reactive to observed glucose levels may be utilized. PID can be tuned based on simple rules of the mathematical models of the metabolic interactions between glucose and insulin in a person. Alternatively, model predictive controllers ("MPC") may be used. The MPC is advantageous because the MPC proactively considers the near future effects of control changes, and is sometimes subject to constraints in determining the output of the MPC, whereas PID typically involves only past outputs in determining future changes. Constraints can be implemented in the MPC such that a solution in a confined "space", meaning within imposed delivery limitations, is guaranteed and the system is prevented from exceeding a limit that has been reached.

Known MPCs are described in the following documents: U.S. Pat. No. 7,060,059; U.S. Patent Publication Nos. 2011/0313680 and 2011/0257627; International Publication WO 2012/051344; Percival et al., "Closed-Loop Control and Advisory Mode Evaluation of an Artificial Pancreatic Beta Cell: Use of Proportional-Integral-Derivative Equivalent Model-Based Controllers" J. Diabetes Sci. Technol., Vol. 2, Issue 4, July 2008; Paola Soru et al., "MPC Based Artificial Pancreas, Strategies for Individualization and Meal Compensation," Annual Reviews in Control 36, p. 118-128 (2012); Cobelli et al., "Artificial Pancreas. Past, Present, Future" Diabetes Vol. 60, November 2011; Magni et al., "Run-to-Run Tuning of Model Predictive Control for Type 1 Diabetes Subjects: In Silico Trial" J. Diabetes Sci. Techn., Vol. 3, Issue 5, September 2009; Lee et al., "A Closed-Loop Artificial Pancreas Using Model Predictive Control and a Sliding Meal Size Estimator" J. Diabetes Sci. Techn., Vol. 3, Issue 5, September 2009; Lee et al., "A Closed-Loop Artificial Pancreas based on MPC: Human Friendly Identification and Automatic Meal Disturbance Rejection," Proceedings of the 17$^{th}$ World Congress, The International Federation of Automatic Control, Seoul Korea Jul. 6-11, 2008; Magni et al., "Model Predictive Control of Type 1 Diabetes: An in Silico Trial" J. Diabetes Sci. Techn., Vol. 1, Issue 6, November 2007; Wang et al., "Automatic Bolus and Adaptive Basal Algorithm for the Artificial Pancreatic β-Cell" Diabetes Techn. Ther., Vol. 12, No. 11, 2010; Percival et al., "Closed-Loop Control of an Artificial Pancreatic β-Cell Using Multi-Parametric Model Predictive Control," Diabetes Res. 2008; Kovatchev et al., "Control to Range for Diabetes: Functionality and Modular Architecture," J. Diabetes Sci. Techn., Vol. 3, Issue 5, September 2009; and Atlas et al., "MD-Logic Artificial Pancreas System," Diabetes Care, Vol. 33, No. 5, May 2010. All articles or documents cited in this application are hereby incorporated by reference into this application as if fully set forth herein.

Glucose control systems conventionally use a measure of insulin-on-board that accounts for all bolus insulin injected without accounting for the difference between insulin injected for meal-related purposes versus that for correction (i.e., glucose concentration-lowering) purposes. In systems that do not have a meal model, two models for insulin-on-board accounting are proposed to improve glucose control: patient-facing insulin-on-board and system-facing insulin-on-board. By "patient-facing insulin-on-board" or "PFIOB" is meant insulin-on-board inclusive of meal-related insulin and correction-related insulin, but generally excluding basal insulin; a well-known value easily understood by patients. By "system-facing insulin-on-board" or "SFIOB" is meant, in a system without a meal model, insulin-on-board that has the potential to lower glucose concentration, i.e., correction-related insulin; this value excludes both meal-related insulin and basal insulin, neither of which are intended to lower glucose concentration. The use of these separate models is problematic in that there is a need to separate meal-related insulin from boluses which may include both meal- and correction-related insulin. The systems solve this problem by the use of accurate therapeutic parameters, such as insulin to carbohydrate ratio and insulin sensitivity factor along with the proper use of a bolus calculator. However, if the system user does not inform the system of meal boluses or correction boluses or omits carbohydrates, blood glucose or both while using the bolus calculator, or increases or decreases the calculated bolus dose without system awareness of the rationale for the increase or decrease, an erroneous increase, reduction or suspension of insulin may occur.

Thus, there is a need in the field to provide a diabetes management system that can utilize a set of rules to overcome this disadvantage.

DETAILED DESCRIPTION

Figure 1:
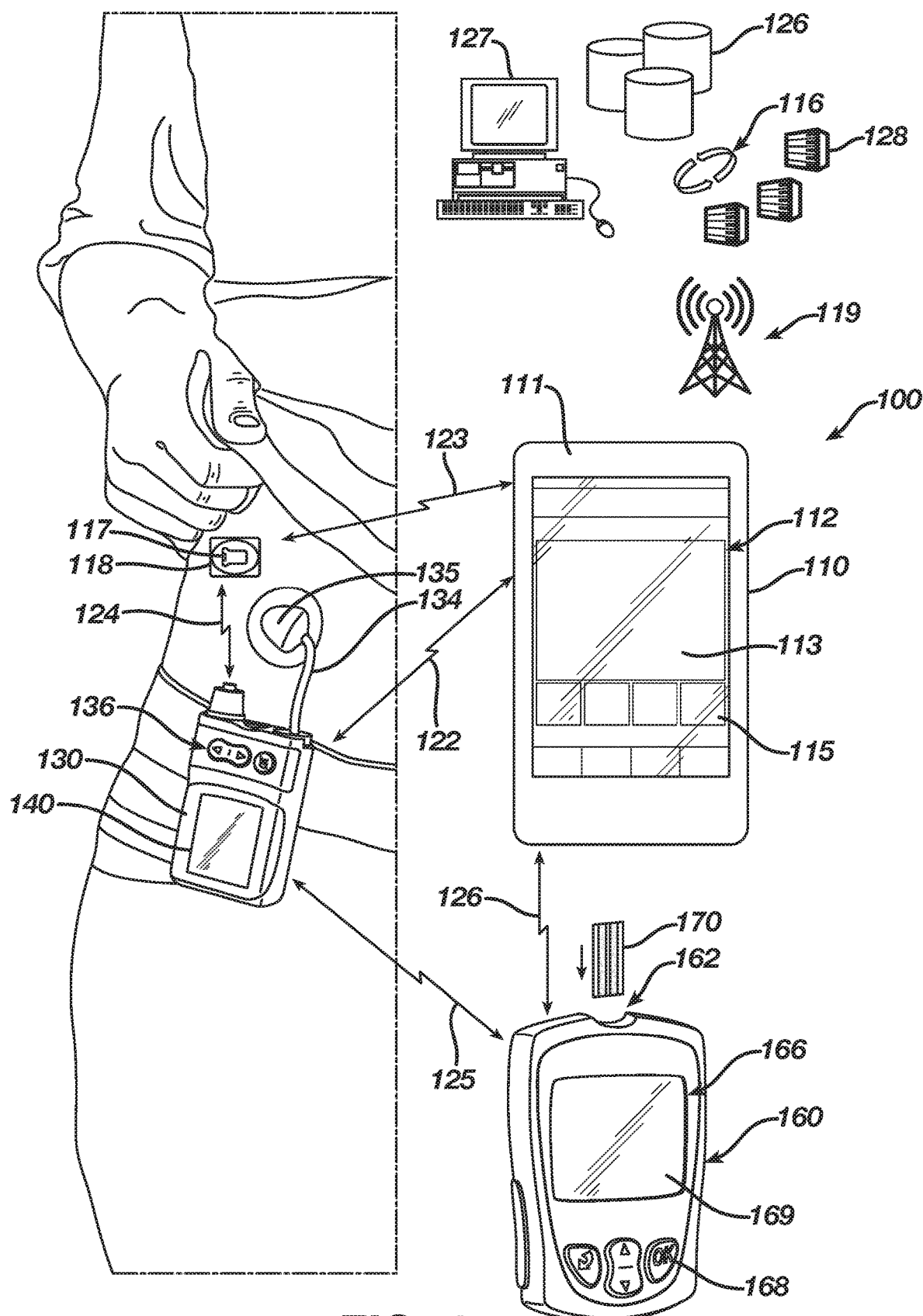
FIG. 1 is a schematic view of an embodiment of an artificial pancreas ("AP") diabetes management system.

A key requirement for the effective implementation of a closed-loop insulin delivery system using a model predictive control algorithm ("MPC") is the determination of, and accurate accounting for, insulin administered to the user that is both currently active in the body and has yet to become active, known as insulin-on-board ("IOB") in the patient or user. This invention provides systems, and methods for use in the systems, in which bolus insulin is accounted for in a way that ensures that the system-facing IOB ("SFIOB") maintains, as accurately as possible, only and all correction insulin (meaning insulin that is administered to lower blood glucose) thus enabling insulin dosing by the system which is both safe and effective.

The glucose management system of the invention includes: a glucose meter that determines a blood glucose ("BG") value for a biological sample; an insulin pump, which is in communication with the meter, and is programmed to deliver a user-initiated insulin bolus to the user; a controller that is coupled to a user interface and includes a processor that is programmed to: (i) determine whether the user has input a blood glucose value into the user interface, (ii) calculate the correction component, meaning the bolus component administered to lower blood glucose, of the bolus based on the blood glucose value; (iii) determine whether the user has input a carbohydrate amount into the user interface; and (iv) calculate a component of the bolus based on the carbohydrate amount (the meal component of the bolus). In the system of the invention, the SFIOB is then determined based on at least one of the correction component and meal component of the bolus. When a glucose value and a carbohydrate value are not entered into the controller, these components can be calculated based on the latest CGM value. If the CGM value is not available either, then one-half (50%) of the total insulin bolus is attributed to SFIOB.

The invention also relates to a method of accounting for insulin-on-board in a glucose measurement system in which a patient-initiated insulin bolus is dosed after which a determination is made as to whether the user input data into the controller pertaining to a previous blood glucose concentration value, as measured by the system. If a previous blood glucose concentration value was entered, then a blood glucose correction component of the bolus is calculated based on that value. A second determination is made as to whether the user has input data into the controller pertaining to a carbohydrate amount. If a carbohydrate amount was entered, then the meal component of the bolus is calculated that is based on that carbohydrate amount. A third determination is made as to whether the user adjusted the insulin bolus that the user initiated. The SFIOB is then determined based on at least one of the calculated bolus components and the third determination or adjusted amount. A predetermined component of one-half (50%) of a total meal-related insulin bolus is attributed to insulin-on-board when the previous blood glucose value and the carbohydrate amount are not input into the controller and the latest CGM value is not available.

The invention also relates to a glucose management system having a sensor that automatically determines a blood glucose value for a biological fluid and an insulin pump that receives data obtained by the sensor and is programmed to deliver a patient or user-initiated insulin bolus to a user. The system also includes a controller that exchanges data with the pump and has a user interface and a processor. The processor is programmed to: determine whether the user has input data into the user interface pertaining to a previous blood glucose value, as measured by the system; calculate the correction component of the bolus based on the previous blood glucose value; determine whether the user has input data into the user interface pertaining to a carbohydrate amount; and calculate the meal component of the bolus based on the carbohydrate amount. The SFIOB is then determined based on at least one of the bolus components. A predetermined correction component of one-half (50%) of the total meal-related insulin bolus is attributed to insulin-on-board when the previous blood glucose value and the carbohydrate amount are not input into the controller and the latest CGM value is not available.

Referring to FIG. 1, an artificial pancreas ("AP") diabetes management system 100 includes a controller 110 and a drug delivery device or insulin pump 130. The drug delivery device 130 is connected to an infusion set 135 via flexible tubing 134. The controller 110 includes a housing 111, a user interface 112, an autonomous modulation (or control) algorithm that may be any suitable control algorithm and preferably is MPC 150 (FIG. 2), and a memory unit (not shown). The drug delivery device 130 is configured to transmit and receive data to and from the controller 110 by, for example, a communications link 122 such as radio frequency, Bluetooth® or the like. In one embodiment, the drug delivery device 130 is an insulin infusion device, or pump, and the controller 110 may be a hand-held portable controller, or a consumer electronic device, such as a smart phone, computer, exercise or user monitoring device, or the like. In such an embodiment, data transmitted from the drug delivery device 130 to the controller 110 may include information such as, for example, insulin delivery data, blood glucose information, basal, bolus, insulin to carbohydrates ratio or insulin sensitivity factor. The controller 110 can be configured to include a closed-loop controller that has been programmed to receive continuous glucose readings from a CGM sensor 117 via a communications link 123. Data transmitted from the controller 110 to the drug delivery device 130 may include glucose test results and a food database to allow the drug delivery device 130 to calculate the amount of insulin to be delivered. Alternatively, the controller 110 may perform basal dosing or bolus calculation and send the results of such calculations to the drug delivery device 130. Bolus calculation may be done manually upon initiation by the subject, or may be automated so that the system is capable of incorporation both bolus and basal insulin control.

Still referring to FIG. 1, a glucose meter 160 (e.g., an episodic blood-glucose meter), alone or in conjunction with the CGM sensor 117, provides data to either or both of the controller 110 and drug delivery device 130, e.g., via respective communication links 123, 124. The glucose meter 160 can measure a fluid sample placed on a test strip 170. The controller 110 can present information and receive commands via user interface, such as the touch screen 113 shown, or other devices.

The controller 110, the drug delivery device 130, and the CGM sensor 117 can be integrated into multi-function units in any combination. For example, the controller 110 can be integrated with the drug delivery device 130 to form a combined device with a single housing. Infusion, sensing, and controlling functions can also be integrated into a monolithic artificial pancreas. In various embodiments, the controller 110 is combined with the glucose meter 160 into an integrated monolithic device having a housing. In other embodiments, the controller 110 and the glucose meter 160 are two separable devices that are dockable with each other to form an integrated device. Each of the devices 130, 110, and 160 has a suitable micro-processor (not shown for brevity) programmed to carry out various functions.

The drug delivery device 130 or the controller 110 can also be configured for bi-directional communication with a remote health monitoring station through, for example, a communication network 119. One or more servers 128 or storage devices 126 can be communicatively connected to the controller 110 via the network 119. In an example, the drug delivery device 130, controller 110, or both may communicate with a personal computer 127 via a communication link, such as radio frequency, Bluetooth®, or the like. The controller 110 and the remote station also can be configured for bi-directional wired communication through, for example, a telephone land-based communication network. Examples of remote monitoring stations may include, but are not limited to, a personal or networked computer 127, a server 128, a memory storage 126, a personal digital assistant, other mobile telephone, a hospital-based monitoring station or a dedicated remote clinical monitoring station. Alternatively and though not shown in FIG. 1, storage may further be provided in the cloud.

Still referring to FIG. 1, the controller 110 also includes a user interface 112. As shown, the user interface 112 has a display screen 113 and one or more actuable buttons 115 which allow the user to turn the controller 110 on and off, as well as manually input data and select various functions of the controller 110. In an embodiment, the user interface 112 may also include an audible alarm, vibrator, or voice prompt to notify the user of a specific operating status or request data from the user. In another embodiment, the user interface 112 includes a touch screen display in addition to the one or more actuable buttons.

The control algorithm can reside in the remote controller 110, in the drug delivery device 130, or both in the configurations shown in FIG. 1. In one configuration, the controller 110 will wirelessly gather the necessary information (e.g., insulin history) from the drug delivery device 130, as well as from the glucose sensor 117 (e.g., glucose data) to allow the drug delivery device 130, using the control algorithm, to calculate the amount of insulin to be modulatively delivered by the drug delivery device 130. Alternatively, the controller 110 includes the control algorithm and may perform basal dosing or bolus calculation, and send the results of such calculations via communications link 122, along with delivery instructions to the drug delivery device 130. In an alternative embodiment, the episodic blood glucose meter 160 and biosensors 170 also may be used alone or in conjunction with the CGM sensor 117 to provide blood glucose data to either or both the controller 110 and the drug delivery device 130.

According to one embodiment, the controller 110 further includes an MPC 150 (FIG. 2), which is programmed to receive continuous data from a CGM sensor 117 via a transmitter 118 that is coupled to the CGM sensor 117 and through a communications link 123. The transmitter 118 transmits data received from the CGM sensor 117 pertaining to the glucose concentration of the user's interstitial fluid. In another embodiment, the controller 110 receives the data from a CGM receiver that is housed in the drug delivery device 130 via communications link 122. The controller 110 can process the data received and transmit additional data to the drug delivery device 130, which may include data related to glucose test results and a food database. The drug delivery device 130 can use the data received from the controller 110 to calculate the amount of insulin to be delivered to the user at a given time point. The controller 110 may also perform basal dosing or calculation of an insulin bolus and transmit such calculations to the drug delivery device 130.

In an embodiment, the controller 110 receives signals from a transmitter 118 connected to a CGM glucose sensor 117 via a communications link 123. The controller 110 has a central processing unit ("CPU") programmed to perform a variety of functions and calculations. The MPC 150 (FIG. 2) is programmed to use the data obtained from the CGM sensor 117 to determine, in one instance, the proper amount of insulin to deliver to the user at predetermined periodic time intervals. The controller 110 then transmits the dosing instructions to the drug delivery device 130, which delivers the calculated amount of insulin through an infusion set 135. The glucose concentration of the interstitial fluid can be correlated to the glucose concentration of blood such that it is not necessary for the user to perform as many finger-sticks to measure blood glucose. Since the controller 110 is programmed to receive data from the transmitter 118 or the CGM receiver (not shown), the controller 110 can also be programmed to approximate blood glucose concentration values using the data, as well as predict blood glucose trends and blood glucose rate of change over time.

Still referring to FIG. 1, the glucose meter 160 further includes a glucose meter user interface 166 which can include one or more actuable buttons 168 and a display screen 169. In a further embodiment, the display screen 169 can have touchscreen capabilities. A test strip port 162 is configured to accept an electrochemical test strip or biosensor 170. The electrochemical test strip 170 is configured at one end to react to a biological sample, such as blood, with a reagent, and establish electrical communication with the glucose meter 160 at the opposite end.

Figure 2:
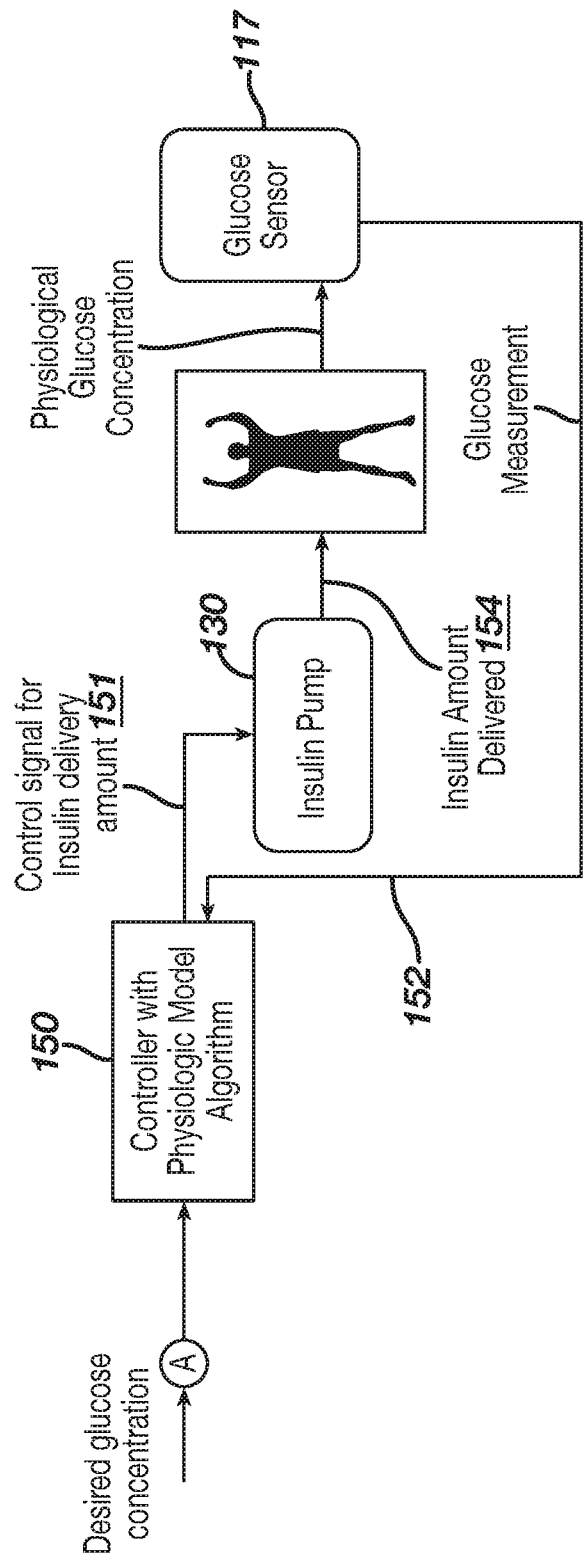
FIG. 2 is a schematic of the core of the AP diabetes management system of FIG. 1.

Referring to FIG. 2, the MPC 150 accesses the glucose concentration data obtained by the CGM sensor 117 or (and preferably) by the glucose meter 160 (FIG. 1) and calculates a correction bolus value, that will be transmitted to the drug delivery device 130 from which the calculated bolus will be dispensed into the user. In an embodiment, the glucose concentration is obtained from the glucose meter via a communications link 126. The controller 110 may also include the memory unit (not shown) that is in communication with the MPC 150. The memory unit (not shown), which can include volatile and non-volatile memory, can store a series of blood glucose values and other related data that may be accessed by the MPC 150 to calculate blood glucose trends and average blood glucose values over a designated period of time and at predetermined time intervals. According to one embodiment, the predetermined time interval is five (5) minutes. In an embodiment, the memory unit) stores predetermined information related to the user's insulin sensitivity factor ("ISF"), carbohydrate ratio ("CR"), target blood glucose concentration ("T"), and other predetermined metabolic parameters. The memory unit can include volatile and non-volatile memory. The MPC 150 is programmed to automatically regulate the rate of insulin delivery to the user based on glucose measurements provided by the CGM sensor 117, data input by the user, and any parameters stored in the memory unit at each predetermined time interval.

The drug delivery device 130 further includes a CPU and a CGM receiver. The CPU is programmed to dispense the proper insulin dose based on instructions received from the controller 110. The CGM receiver is programmed to receive data from the transmitter 118 and transmit or relay said data to the controller 110. In an embodiment, the drug delivery device 130 has one or more actuable buttons or dials 136 that allow the user to input data into the drug delivery device 130. The drug delivery device can also include a drug delivery display screen 140 that relays visual information to the user, which display screen 140 may have touchscreen capabilities. The data input into the drug delivery device 130 by the user can include programming a patient-initiated insulin bolus.

The glucose sensor 117 is an electrochemical sensor that measures the glucose concentration of the user's interstitial fluid at predetermined time intervals and transmits these data back to the controller 110 (or the CGM receiver housed in a separate drug delivery device 130) via a transmitter 118. Blood glucose concentrations can be approximated using data obtained by the glucose sensor 117 and transmitted via the transmitter 118 to the controller 110 or CGM receiver housed in a separate drug delivery device 130. The controller 110 receives information from the transmitter 118 and calculates the proper insulin dose to administer to the user and transmits these dosing instructions to the drug delivery device 130. The controller 110 may also transmit and receive data over a communication network 119 such that data pertaining to the user's therapy can be accessed by medical professionals or other individuals or entities over the Internet, or any other information network.

Referring to FIG. 2, the first output 151 of the MPC 150 can be instructions to an insulin pump or drug delivery device 130 to deliver a desired quantity of insulin 154 to achieve a desired glucose concentration, into the user at the next predetermined time (where such time intervals can be, for example, five minutes). As noted, the glucose sensor 117 measures glucose levels of the user's interstitial fluid and this information is used to estimate the user's actual blood glucose level.

The logic described above and depicted schematically in FIG. 2 relies on predicted glucose concentration levels based on previous information entered into the AP system 100 (FIG. 1) via communication with other AP system 100 components or the user. Absent the proper information, the MPC 150 cannot provide accurate predictions and therefore can cause improper corrections or refinements to the drug delivery device 130. For example, current AP systems having a model predictive control algorithm do not accurately parse meal-related versus correction-related IOB, resulting in fundamentally misinformed predictions of future blood glucose concentrations.

Currently, there are three (3) recognized methods for accounting for IOB after a patient-initiated insulin bolus is delivered: (1) classify none of the insulin bolus as IOB; (2) classify all of the insulin bolus as IOB; or (3) classify one-half (50%) of the insulin bolus as IOB. However, the present invention provides a technique to more accurately determine or classify the amount of an insulin bolus that is required to correct for carbohydrate ingestion ("CHO") and the amount that is required to correct for suboptimal blood glucose concentration ("BG")

Figure 3:
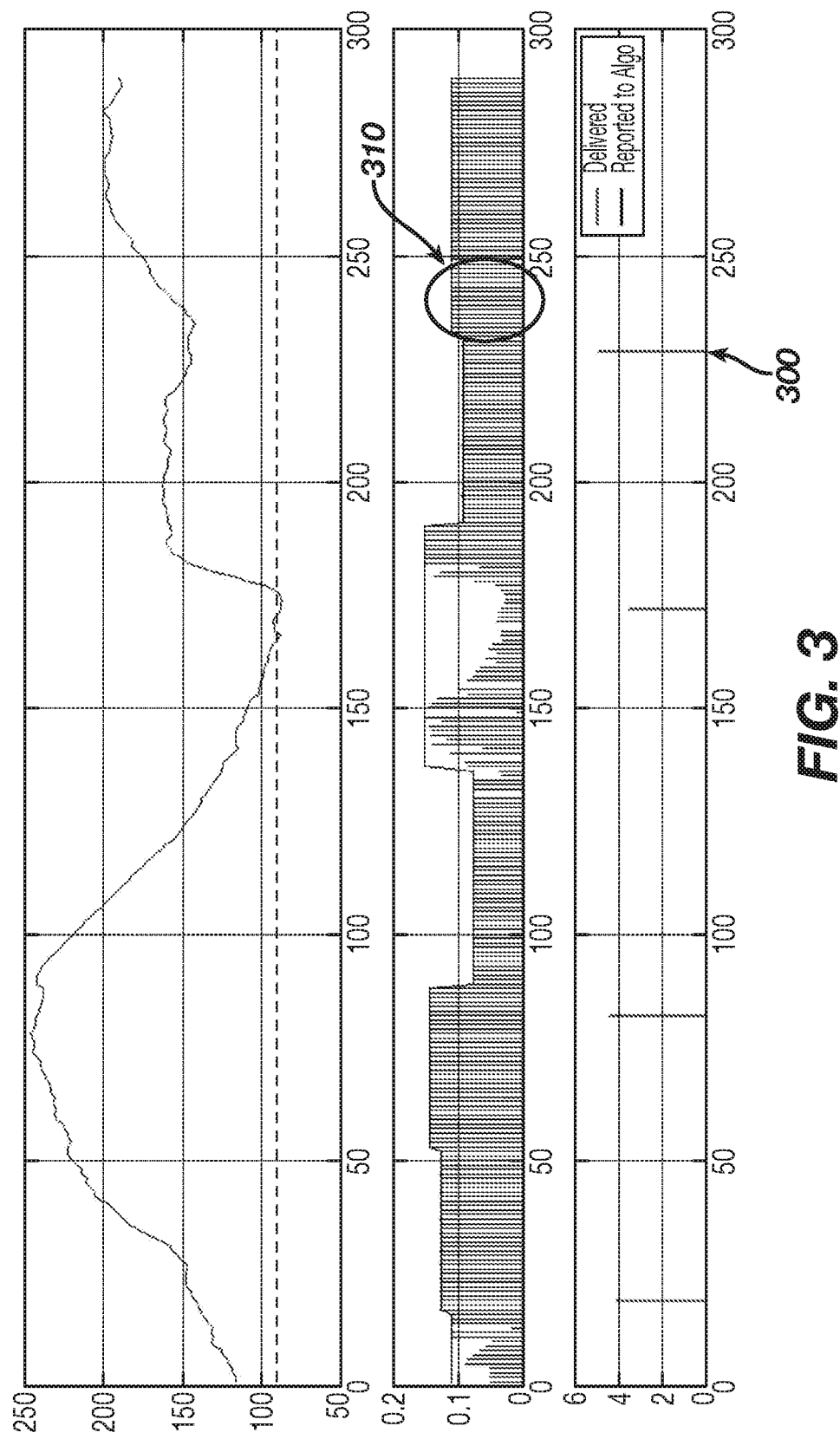
FIG. 3 is a graph of insulin delivery in an embodiment of an AP system after a patient-initiated insulin bolus in which none of the insulin is reported as insulin-on-board.

Method 1, as shown in FIG. 3, is characterized by the user administering an insulin bolus 300 in conjunction with a meal and not reporting any of it to the MPC 150 (FIG. 2) as IOB. Accordingly, the AP system 100 (FIG. 1) does not take the insulin bolus 300 into account and therefore, does not predict a decrease in blood glucose concentration in the near future 310 following administering of the insulin bolus 300 and provides an improper prediction to the AP system 100 (FIG. 1). The "near future" or "post-delivery period" is defined as the period of time directly following administration of the insulin bolus 300 during which the absorption of the corresponding meal significantly affects the glucose concentration. The prediction provided by the MPC 150 (FIG. 1) to the system 100 (FIG. 1) will be an overestimation of the amount of insulin that should be administered by the drug delivery device 130 (FIG. 1) in the post-delivery period. Accordingly, the correction or refinement to the user's insulin delivery determined by the system will not lead to the proper decrease in insulin delivery and can result in an insulin-induced hypoglycemic event as too much insulin is delivered to the user and their blood glucose levels fall below the predetermined range or target. As shown in FIG. 3, the insulin delivery by the system still remains high in the near future 310 following the unreported insulin bolus.

Figure 4:
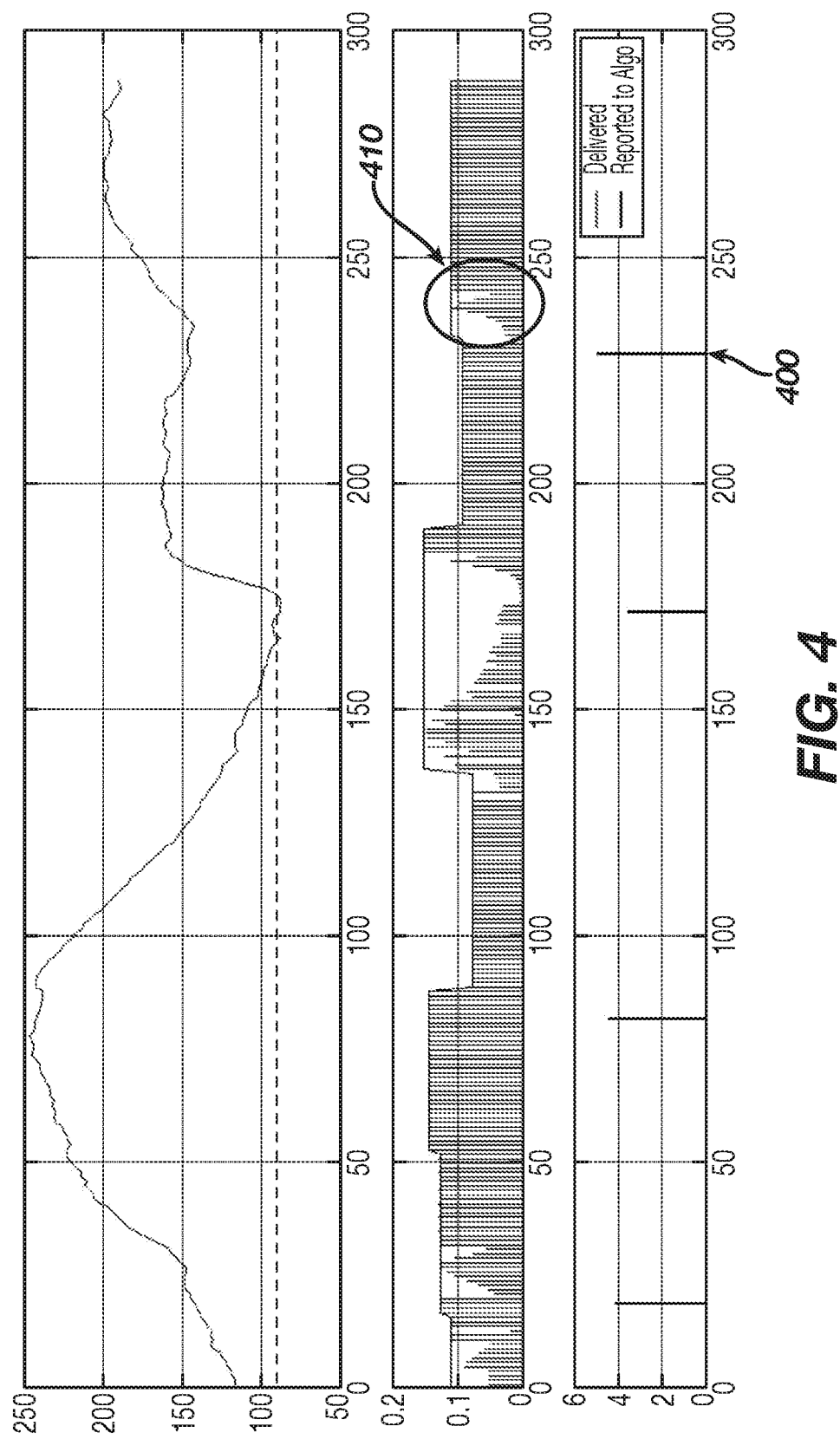
FIG. 4 is a graph of insulin delivery in an embodiment of an AP system after a patient-initiated insulin bolus in which all of the insulin is reported as insulin-on-board.

Method 2, as shown in FIG. 4, is characterized by the user administering an insulin bolus 400 in conjunction with a meal and reporting the entire insulin bolus 400 to the MPC 150 (FIG. 2) as IOB. However, only a portion of the insulin bolus 400 is a meal component required to correct for the carbohydrate ingestion and the other portion is used for a correction component to correct the user's blood glucose in the normal course. Therefore, the MPC 150 (FIG. 2) will recognize an artificially high SFIOB and will predict a drastic decrease in blood glucose concentration during the post-delivery period 410. Consequently, the modification of the user's basal insulin delivery provided by the AP system 100 (FIG. 1) will amount to a decrease (or even a suspension) of insulin delivery in the near future following the delivery of the insulin bolus 400. This will result in the user's blood glucose levels increasing above T and may cause a hyperglycemic event. As shown in FIG. 4, the insulin delivery in the near future 410 by the system is significantly decreased following the reported insulin bolus 400. The amount of insulin delivered in the near future 410 is also seen to oscillate which would correspond to an oscillation in the user's blood glucose levels as the system 100 (FIG. 1) attempts to reestablish the basal levels of insulin delivery.

Method 3 classifies one-half (50%), or some other predetermined percentage of the patient-initiated insulin bolus, as IOB. However, the system 100 (FIG. 1) can still deliver much more or much less insulin than is required to keep the user's blood glucose in check during the post-delivery period. Accordingly, the user will still experience a higher frequency of suboptimal glucose levels than with the method disclosed. The results of each alternative method are compared with the results of the current method in Examples 1-6, which are discussed further below.

Figure 5:
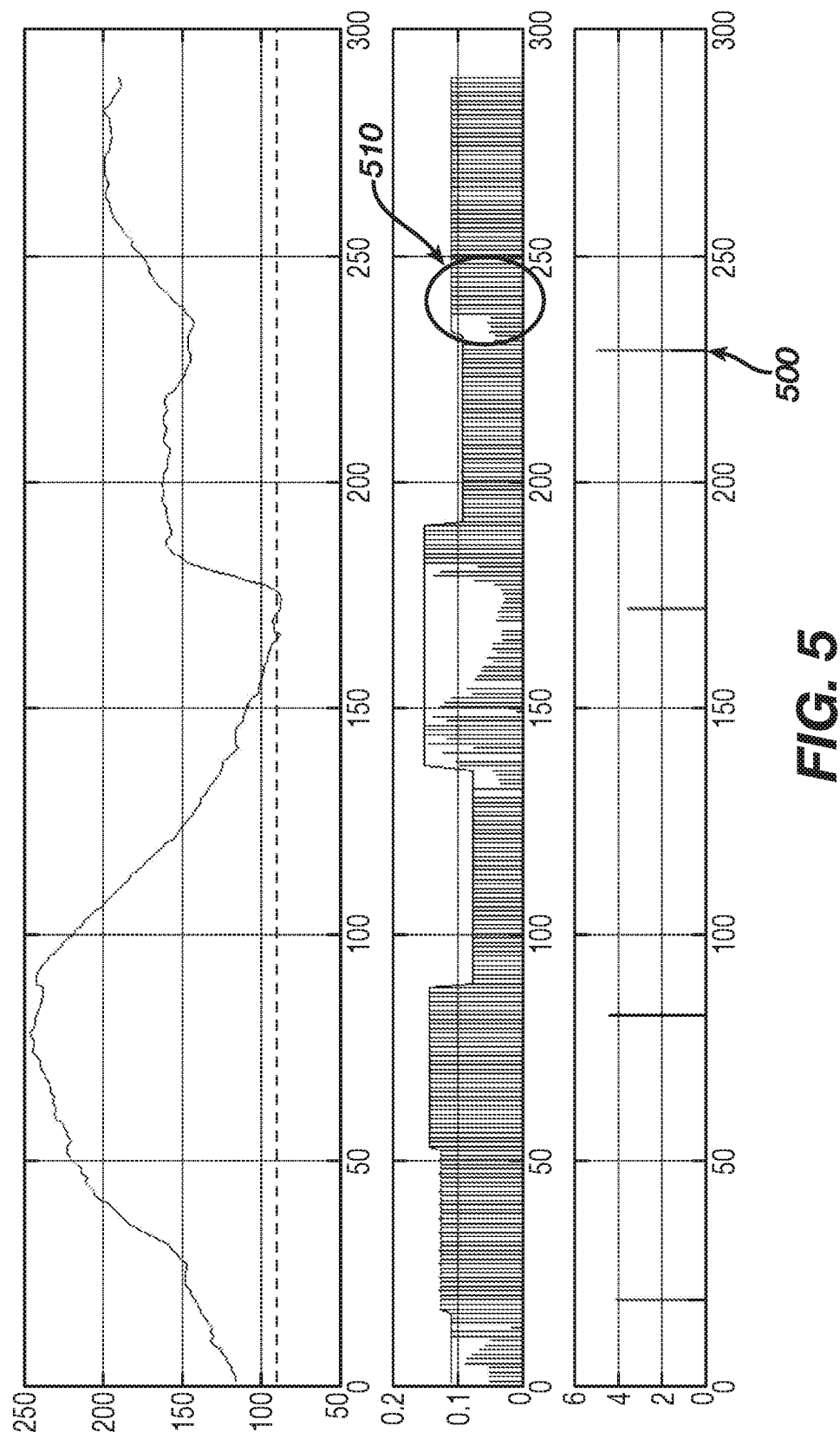
FIG. 5 is a graph of insulin delivery of an embodiment of the claimed AP system after a patient-initiated insulin bolus in which some of the insulin is reported as insulin-on-board.

The current AP system 100 (FIG. 1) uses an MPC 150 (FIG. 2) that is programmed to account for SFIOB in order to prevent the large increases and decreases in blood glucose concentration that occur in the systems of FIGS. 3 and 4, previously discussed. Referring to FIG. 5, the MPC 150 (FIG. 2) is programmed to only classify a portion of the insulin bolus 500 that is delivered to the user as SFIOB and therefore, only takes this portion of insulin into account when predicting glucose levels in the near future 510. Upon comparing insulin delivery in the near future 310, 410, and 510 from the systems of FIGS. 3-5, post-delivery insulin administration at 510 is more regulated and falls between the levels seen at 310 (which would possibly result in a hypoglycemic event) and 410 (which would possibly result in a hyperglycemic event).

Figure 6:
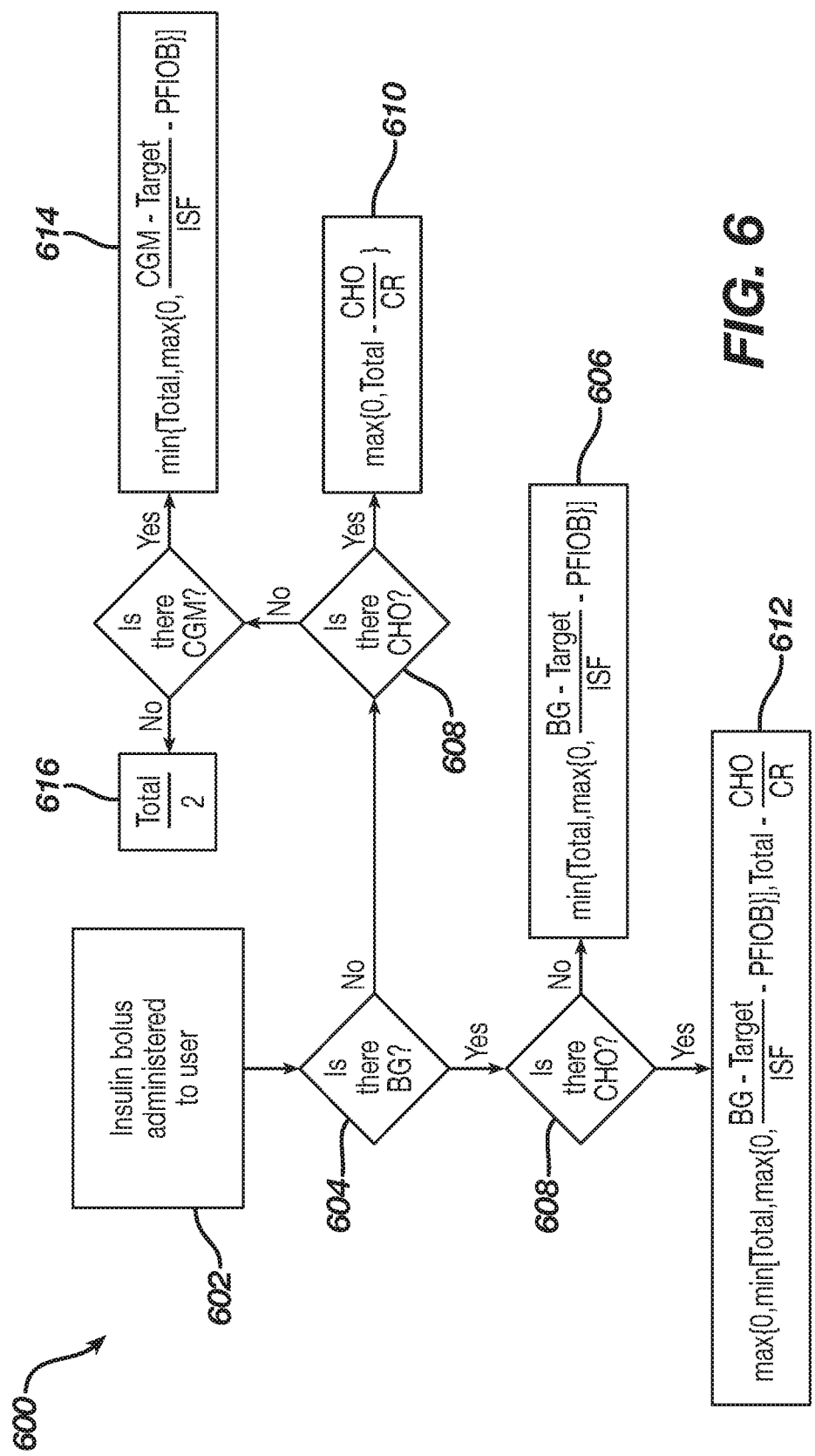
FIG. 6 is a flow chart of the bolus parsing logic of an embodiment of an AP diabetes management system.

The MPC 150 (FIG. 2) determines what data has been received from the other parts of the system 100 (FIG. 1) and what assumptions, if any, it will need to make in order to classify a part of the patient-initiated insulin bolus as being attributed to SFIOB. Referring to flow chart 600 of FIG. 6, the patient-initiated bolus is administered at step 602. At step 604, the algorithm then determines whether a BG value is available—either entered manually by the user or populated automatically by the blood glucose meter via a communication link 126 (FIG. 1). Once the MPC 150 (FIG. 2) determines whether a BG value is available, the MPC then determines whether a CHO was provided by the user at step 608. The CHO value corresponds to an estimate of the carbohydrate amount in the food that the user is about to eat or is currently eating.

If a BG value is available, while a carbohydrate amount is not available, then the amount of insulin intended to correct for high BG value, or the BG correction insulin amount, is determined at step 606 using the formula below:

$$\min\left\{\text{Total}, \max\left[0, \frac{BG - \text{Target}}{ISF} - PFIOB\right]\right\} \quad (1)$$

wherein "min" is the minimum function;
"max" is the maximum function;
"Total" is the total bolus; "Target" is the glucose target of the patient; and
"ISF" is the insulin sensitivity factor of the patient.

If a CHO value is provided by the user, while a BG value is not available, then the amount of insulin intended to correct for high BG is calculated at step 610 using the formula below:

$$\max\left\{0, \text{Total} - \left(\frac{CHO}{CR}\right)\right\} \quad (2)$$

wherein "CR" is the user's carbohydrate ratio.

When both a BG value and a CHO value are available, then the insulin amount intended for correction is calculated at step 612 using the following formula:

$$\max\left\{0, \min\left[\text{Total}, \max\left\{0, \frac{BG - \text{Target}}{ISF} - PFIOB\right\}\right], \text{Total} - \frac{CHO}{CR}\right\} \quad (3)$$

It is beneficial to err on the conservative side in the amount of insulin delivered to the user in order to prevent insulin-induced hypoglycemic events. For example, when there are two or more methods to calculate the IOB, the method that produces the larger number will result in the MPC 150 (FIG. 2) providing a lower blood glucose prediction to Junction A. This will make the controller 110 (FIG. 1) suggest a more conservative insulin regimen or correction component in the near future (i.e. delivering less insulin than may be required).

When neither BG, nor CHO amounts are available, the CGM value may be substituted at step 614 for BG. The resulting correction value for SFIOB is then determined using the following relation:

$$\min\left\{\text{Total}, \max\left[0, \frac{CGM - \text{Target}}{ISF} - PFIOB\right]\right\} \quad (4)$$

In the case when CGM data is also not readily available, the algorithm reverts to the 50%/50% approach and calculates the intended correction using the following relation (616 of FIG. 6):

$$\frac{\text{Total}}{2} \quad (5)$$

The following examples are provided to demonstrate the described methodology:

EXAMPLES

Example 1

The following values are predetermined and stored in the memory unit (not shown) of the drug delivery device 130:
The user's CR is 10 grams per unit of insulin;
The user's ISF is 50 mg/dl per unit of insulin;
The user's target blood glucose value is 120 mg/dl; and
The current PFIOB is 0.

According to this Example, the user did not enter a blood glucose (BG) value but did provide an estimate of the amount of carbohydrates taken in at a meal as 20 g. The MPC 150 (FIG. 2) calculates the CHO insulin amount as follows:

$$\frac{20 \text{ g}}{10 \text{ g/unit}} = 2 \text{ units of insulin}$$

However, the user then manually increases the dose to 3 units of insulin. The controller 110 is programmed such that it trusts that the user estimated their entered carbohydrate amount as correctly as possible. Therefore, the MPC 150 (FIG. 2) can correctly attribute 2 units of insulin as accounting for the increase in glucose to be expected after the user consumes their 20 g of carbohydrates. In this instance, the algorithm determines the correction insulin that is the difference between the total bolus amount and the carbohydrate bolus calculated by the controller and based on the carbohydrate amount entered by the user.

Correction: 3 units delivered−2 units calculated=1 unit

The MPC 150 (FIG. 2) therefore classifies one (1) unit of insulin as a correction component for correcting the user's BG value and two (2) units of insulin as a meal component for meal coverage. Accordingly, only one unit of insulin is classified as SFIOB going forward and is taken into account by the MPC 150 (FIG. 2) when predicting glucose concentration for the purposes of insulin administration in the near future or post-delivery period. This result can be compared to methods 1-3, which were previously discussed and examples of which are shown in FIGS. 3-5. As shown below, utilizing any one of the previous methods results in below optimal or above optimal insulin delivery in the near future as compared to the claimed method.

| Method 1 | Method 2 | Method 3 | Claimed Method |
| --- | --- | --- | --- |
| 0 units | 3 units | 1.5 units | 1 unit |

Example 2

Using the same stored parameters as Example 1, the user again estimates their carbohydrate intake to be 20 g. As in Example 1, the controller 110 calculates that two (2) units of insulin is the CHO insulin and should be delivered to the user to account for the CHO value. However, in this instance the user reduces the bolus from two (2) units to one (1) unit.

Correction: 1 unit delivered−2 units calculated=−1 unit

The resulting bolus is a negative number, which means that none of the insulin to be delivered to the user will be classified as correction by the MPC 150 (FIG. 2) since an insulin amount cannot be less than zero. As shown below, only method 1 would attribute the same number of units of insulin as SFIOB for the purposes of the MPC 150 (FIG. 2) predicting glucose levels in the near future as compared to the claimed method.

| Method 1 | Method 2 | Method 3 | Claimed Method |
| --- | --- | --- | --- |
| 0 units | 1 units | 0.5 units | 0 units |

Example 3

Using the same stored information as in Examples 1 and 2, the user enters a BG value of 270 mg/dl into the controller and does not enter a CHO value. The MPC 150 (FIG. 2) determines the BG correction insulin as follows:

$$\frac{270\frac{mg}{dl} - 120\frac{mg}{dl}}{50 \text{ mg/dl}} - 0 = 3 \text{ units of insulin}$$

The user then manually increases the total bolus to five (5) units of insulin. The MPC 150 (FIG. 2) is programmed such that it trusts that the user correctly determined the blood glucose value entered into the controller 110. Therefore, the MPC 150 (FIG. 2) can correctly attribute three (3) units of insulin that is the correction component for correcting the user's elevated blood glucose level. The correction amount in this case is the minimum between the total bolus (5 units) and the correction component based on user-entered BG value (3 units):

Correction: min(5 units total, 3 units calculated)=3 units

The two (2) units of insulin are not taken into account by the MPC 150 (FIG. 2) going forward as the system believes the user increased the total dose for the purpose of possible carbohydrate ingestion and intended a correction only according to the BG value that the user entered (or BG value wirelessly transmitted by the BGM). As shown below, utilizing any one of the previous methods results in below optimal or above optimal insulin delivery in the near future as compared to the claimed method.

| Method 1 | Method 2 | Method 3 | Claimed Method |
| --- | --- | --- | --- |
| 0 units | 5 units | 2.5 units | 3 units |

Example 4

Using the same stored information as in Examples 1-3 and the same BG value as Example 3, the user then manually decreases the total bolus to be delivered to one (1) unit of insulin. The MPC 150 (FIG. 2) is programmed such that it trusts that the user correctly determined the blood glucose value entered in to the controller 110. However, since the total bolus amount is one (1) unit of insulin, MPC 150 (FIG. 2) can only classify the one (1) unit as a correction component and not the calculated 3 units of correction calculated based on the BG value and the user's CF and Target values. In this example, only method 2 would classify the same number of units of insulin as correction for the purposes of the MPC 150 (FIG. 2) predicting glucose levels in the near future as compared to the claimed method.

| Method 1 | Method 2 | Method 3 | Claimed Method |
| --- | --- | --- | --- |
| 0 units | 1 unit | 0.5 units | 1 units |

Example 5

Using the same stored information as in the above examples, the user enters a BG value of 170 mg/dl and a carbohydrate value of 20 g. The MPC 150 (FIG. 2) determines the BG correction insulin as follows:

$$\frac{170\frac{mg}{dl} - 120\frac{mg}{dl}}{50 \text{ mg/dl}} - 0 = 1 \text{ unit of insulin}$$

The MPC 150 (FIG. 2) determines the CHO insulin amount as follows:

$$\frac{20 \text{ g}}{10 \text{ g/unit}} = 2 \text{ units of insulin}$$

Based on the above calculations, the total insulin bolus determined by the MPC 150 (FIG. 2) is three (3) units.

However, in this example, the user increases the total bolus amount from three (3) units to five (5) units. The MPC 150 (FIG. 2) determines the correction component as the maximum between the correction calculated based on BG and CF, which is 1 unit, and the difference between the total insulin bolus (5 units) and the calculated CHO insulin amount (2 units), which is 3 units. These three (3) units of insulin are classified as SFIOB going forward and are taken into account when the system predicts glucose concentration for the purposes of insulin administration during the post-delivery period. In this example, none of the methods classify the same number of units of insulin as correction for the purposes of the MPC 150 predicting glucose levels in the near future as compared to the claimed method.

| Method 1 | Method 2 | Method 3 | Claimed Method |
|---|---|---|---|
| 0 units | 5 units | 2.5 units | 3 units |

Example 6

Using the same stored information as in the above examples, the user enters a BG value of 220 mg/dl and a carbohydrate value of 20 g. The MPC 150 (FIG. 2) determines BG correction as follows:

$$\frac{220\frac{mg}{dl} - 120\frac{mg}{dl}}{50 \text{ mg/dl}} - 0 = 2 \text{ unit of insulin}$$

The MPC 150 (FIG. 2) determines CHO insulin amount as follows:

$$\frac{20 \text{ g}}{10 \text{ g/unit}} = 2 \text{ units of insulin}$$

Based on the above calculations, the total insulin bolus determined by the MPC 150 (FIG. 2) is four (4) units. In this example, the user decreases the amount of the bolus from four (4) units to three (3) units. Since the user entered a BG value, the algorithm assumes that this BG value is accurate and classifies two (2) units as a correction component going forward and this value is taken into account when the system predicts glucose concentration for the purposes of insulin administration during the post-delivery period. As shown below, utilizing any one of the previous methods results in below optimal or above optimal insulin delivery in the near future as compared to the claimed method.

| Method 1 | Method 2 | Method 3 | Claimed Method |
|---|---|---|---|
| 0 units | 3 units | 1.5 units | 2 units |

Additional embodiments include any of the embodiments described above and described in any and all exhibits and other materials submitted herewith, where one or more of its components, functionalities, or structures is interchanged with, replaced by, or augmented by one or more of the components, functionalities, or structures of a different embodiment described above.

It should be understood that various changes and modifications to the embodiments described herein will be apparent to those skilled in the art. Such changes and modifications can be made without departing from the spirit and scope of the present disclosure and without diminishing its intended advantages. It is therefore intended that such changes and modifications be covered by the appended claims.

What is claimed is:

1. A method of accounting for insulin-on-board in a glucose measurement system, the system including a controller, the method comprising:
   first calculating a system calculated bolus amount;
   after calculating the system calculated bolus amount, then administering to a user a user-initiated insulin bolus amount;
   after administering to a user, then determining whether the user input into the controller a blood glucose concentration value (BG);
   after determining whether the user input into the controller the BG concentration value, next determining whether the user input into the controller a carbohydrate value (CHO);
   if it is determined by the controller that the user input the BG concentration value into the controller, but did not input the CHO value, then calculating a blood glucose correction component of the user-initiated insulin bolus amount based on the BG concentration value;
   if it is determined that the user did not input the BG concentration value into the controller, but did input the CHO value, then using the controller calculating a meal component of the user-initiated insulin bolus amount based on the CHO value;
   after determining whether the user input into the controller the BG concentration and CHO values, then determining whether the system calculated bolus amount and the user-initiated insulin bolus amount are of equal amounts or whether the user-initiated insulin bolus amount is an adjusted bolus amount that is different from the system calculated bolus amount; and
   subsequently using the controller to determine a system-facing insulin-on-board value based on at least one of the blood glucose correction component, meal component, and the adjusted bolus amount; and
   wherein if all of the BG concentration value, CHO value and a continuous glucose measurement (CGM) value are not available, then the system-facing-insulin-on-board is then calculated by the controller to be the blood glucose correction component calculated as a predetermined percentage of the user-initiated insulin bolus amount.

2. The method of claim 1, wherein if it is determined that the BG concentration value was input into the controller, and the CHO value was not input, then the blood glucose correction component is calculated by the controller as:

$$\min\left\{\text{Total}, \max\left[0, \frac{BG - \text{Target}}{ISF} - PFIOB\right]\right\}$$

where Total is a total amount of the user-initiated insulin bolus amount, Target is a target blood glucose value, ISF is a predetermined insulin sensitivity factor and PFIOB is a patient-facing insulin-on-board value.

3. The method of claim 2, wherein the target blood glucose value is predetermined by the controller and stored in a memory unit of the controller.

4. The method of claim 2, wherein the predetermined insulin sensitivity factor is stored in a memory component of the controller.

5. The method of claim 1, wherein if it is determined that the BG concentration value was not input into the controller and, the CHO value was input, then the blood glucose correction component of the user-initiated insulin bolus amount is calculated by the controller as:

$$\max\left\{0, \text{Total} - \left(\frac{CHO}{CR}\right)\right\}$$

where Total is a total amount of the user-initiated insulin bolus amount and CR is a predetermined ratio of grams of carbohydrate to units of insulin.

6. The method of claim 1, wherein if it is determined that both BG and CHO values were input, then the blood glucose correction component of the user-initiated insulin bolus amount is calculated by the controller as:

$$\max\left\{0, \min\left[\text{Total}, \max\left\{0, \frac{BG - \text{Target}}{ISF}\right\}\right], \text{Total} - \left(\frac{CHO}{CR}\right)\right\}$$

where Total is a total amount of the user-initiated insulin bolus amount, Target is a target blood glucose value, ISF is a predetermined insulin sensitivity factor and CR is a predetermined ratio of grams of carbohydrate to units of insulin.

7. The method of claim 1, wherein if it is determined that neither BG nor CHO values were input, then the blood glucose correction component of the user-initiated insulin bolus amount is calculated by the controller based on the continuous glucose measurement value (CGM) as:

$$\min\left\{\text{Total}, \max\left[0, \frac{CGM - \text{Target}}{ISF} - PFIOB\right]\right\}$$

where Total is a total amount of the user-initiated insulin bolus amount, Target is a target blood glucose value, CGM is the continuous glucose measurement value, ISF is a predetermined insulin sensitivity factor, and PFIOB is a patient-facing insulin-on-board value.

8. The method of claim 1, in which if it is determined that none of the BG, CHO, and CGM values are available, then the blood glucose correction component of the user-initiated insulin bolus amount is calculated as:

$$\frac{\text{Total}}{2}$$

where Total is a total amount of the user-initiated bolus.

9. The method of claim 1, wherein the user manually adjusts the user-initiated insulin bolus amount.

10. A method of determining a correction component for insulin-on-board in a glucose measurement system, the method comprising:
first delivering a user-initiated insulin bolus amount to a user through a pump;
after delivering the user-initiated insulin bolus amount to the user, then determining whether a controller of the system has received data from the pump pertaining to a blood glucose concentration value (BG);
after determining whether the controller has received data from the pump pertaining to the BG concentration value, next determining whether the controller of the system has received data pertaining to a carbohydrate value (CHO);
if the controller has received data from the pump pertaining to the BG concentration value and has not received data pertaining to the CHO value, then using the controller to calculate a blood glucose correction component of the user-initiated insulin bolus based on the BG concentration value received by the controller;
if the controller has not received data from the pump pertaining to the BG concentration value and has received data pertaining to the CHO value, then using the controller to calculate a meal component of the user-initiated insulin bolus amount based on the CHO value; and
then determining using the controller a system-facing insulin-on-board value based on at least the blood glucose correction component and the meal component of the user-initiated insulin bolus amount,
wherein a predetermined percentage of a total user-initiated insulin bolus amount is attributed to the system-facing insulin-on-board value when both the blood concentration glucose value and the carbohydrate value are not received by the controller.

11. The method of claim 10, further comprising determining whether a user adjusted the user-initiated insulin bolus amount by an adjusted amount and determining using the controller the system-facing insulin-on-board based on at least one of the blood glucose correction component, meal component, and the adjusted amount of the user-initiated insulin bolus amount.

12. The method of claim 10, wherein a continuous glucose measurement value (CGM) is used by the controller for the blood glucose correction component if the BG concentration and the CHO values are not input into the controller.

13. The method of claim 12, the wherein if BG concentration and CHO values are not available, then the blood glucose correction component of the user-initiated insulin bolus amount is calculated by the controller as:

$$\min\left\{\text{Total}, \max\left[0, \frac{CGM - \text{Target}}{ISF} - PFIOB\right]\right\}$$

where Total is a total amount of the user-initiated insulin bolus amount, CGM is a continuous glucose measurement value, Target is a target blood glucose value, ISF is a predetermined insulin sensitivity factor and PFIOB is a patient-facing insulin-on-board value.

14. The method of claim 12, wherein if none of BG, CHO, and the CGM values are available, then the blood glucose correction component of the user-initiated insulin bolus amount is calculated by the controller as:

$$\frac{\text{Total}}{2}$$

where Total is a total amount of the user-initiated insulin bolus amount.

15. The method of claim 10, in which the blood glucose correction component of the user-initiated insulin bolus amount accounts for the BG concentration value received from the pump and a user target blood glucose value, and the blood glucose correction component is calculated by the controller as:

$$\min\left\{Total, \max\left[0, \frac{BG - Target}{ISF} - PFIOB\right]\right\}$$

where Total is a total amount of the user-initiated bolus, Target is the user target blood glucose value, ISF is a predetermined insulin sensitivity factor and PFIOB is a patient-facing insulin-on-board value.

16. The method of claim 15, wherein the target blood glucose value and the insulin sensitivity factor are predetermined values stored in the controller.

17. The method of claim 10, wherein the meal component of the user-initiated insulin bolus accounts for the carbohydrate value (CHO), and the blood glucose correction component of the user-initiated insulin bolus amount is calculated by the controller as:

$$\text{Max}\left\{0, Total - \left(\frac{CHO}{CR}\right)\right\}$$

where Total is a total amount of the user-initiated bolus and CR is a predetermined ratio of grams of carbohydrate to units of insulin.

18. The method of claim 10, wherein if both BG concentration and CHO values are input, then the blood glucose correction component of the user-initiated bolus amount is calculated by the controller as:

$$\max\left\{0, \min\left[Total, \max\left\{0, \frac{BG - Target}{ISF} - PFIOB\right\}\right], Total - \left(\frac{CHO}{CR}\right)\right\}$$

where Total is a total amount of the user-initiated insulin bolus amount, Target is a user target blood glucose value, ISF is a predetermined insulin sensitivity factor, PFIOB is a patient-facing insulin-on-board value, and CR is a predetermined ratio of grams of carbohydrate to units of insulin.

19. The method of claim 10, wherein the user-initiated insulin bolus amount is manually adjustable by a user.

20. A glucose management system comprising:
a sensor positioned subcutaneously in a user;
a drug delivery device configured to exchange data with the sensor and programmed to deliver a user-initiated insulin bolus amount to the user; and
a controller configured to exchange data with the drug delivery device, the controller comprising:
    a user interface, and
    a processor coupled to the user interface and configured to calculate the user-initiated insulin bolus amount, wherein the processor is programmed to:
        first determine whether the user has input data into the user interface pertaining to a blood glucose (BG) concentration value, as measured by the glucose management system,
        then determine whether the user has input data into the user interface pertaining to a carbohydrate value (CHO);
        then calculate a blood glucose correction component of the user-initiated insulin bolus amount based on the blood glucose concentration value, if it is first determined that the user has input data pertaining to a BG concentration value, but has not input data pertaining to a CHO value, and
        then calculate a meal component of the user-initiated insulin bolus amount based on the CHO value, if it is first determined that the user has input data pertaining to the CHO value, but has not input data pertaining to a BG concentration value,
        then determine a system-facing insulin-on-board value based on the at least one of the components of the user-initiated insulin bolus amount,
    wherein a continuous glucose measurement value (CGM) is used when it is determined by the controller that the BG concentration value and the CHO value are not input into the controller, and
    wherein a predetermined percentage of a total insulin bolus is attributed to the system-facing insulin-on-board when the BG concentration value and the CHO value are not input into the controller and the CGM value is not available.

21. The glucose management system of claim 20, wherein the processor is further programmed to determine whether the user increased the user-initiated insulin bolus amount by an adjusted amount and determining the system-facing insulin-on-board based on at least one of the blood glucose correction component, the meal component and the adjusted amount of the user-initiated insulin bolus amount.

* * * * *